United States Patent [19]

Ascione et al.

[11] Patent Number: 5,753,209
[45] Date of Patent: May 19, 1998

[54] PHOTOPROTECTIVE/COSMETIC COMPOSITIONS COMPRISING SYNERGISTIC ADMIXTURE OF SUNSCREEN COMPOUNDS

[75] Inventors: Jean-Marc Ascione, Paris; Anne-Marie Pisson, Brunoy, both of France

[73] Assignee: Société L'Oréal S.A., Paris, France

[21] Appl. No.: 645,152

[22] Filed: May 13, 1996

[30] Foreign Application Priority Data

May 12, 1995 [FR] France .................. 95 05677

[51] Int. Cl.$^6$ .................. A61K 7/40; A61K 7/42; A61K 7/44; A61K 7/00
[52] U.S. Cl. .................. 424/59; 464/60; 464/400; 464/401
[58] Field of Search .................. 424/59, 60, 400, 424/401

[56] References Cited

FOREIGN PATENT DOCUMENTS

| 2642968 | 8/1990 | France . |
| 2695560 | 3/1994 | France . |
| 95/00111 | 1/1995 | WIPO . |

*Primary Examiner*—Shelley A. Dodson
*Attorney, Agent, or Firm*—Burns, Doane, Swecker & Mathis, L.L.P.

[57] ABSTRACT

Topically applicable sunscreen/cosmetic compositions well suited for enhanced photoprotection of human skin and/or hair against the damaging effects of UV-A and UV-B irradiation, particularly solar radiation, comprise a photoprotecting synergistically effective amount of (i) 1,4-benzene [di(3-methylidene-10-camphosulfonic)] acid, optionally either partially or totally neutralized, together with a photoprotecting synergistically effective amount of (ii) a benzotriazole-substituted polyorganosiloxane, in a cosmetically acceptable vehicle, diluent or carrier therefor.

27 Claims, No Drawings

PHOTOPROTECTIVE/COSMETIC COMPOSITIONS COMPRISING SYNERGISTIC ADMIXTURE OF SUNSCREEN COMPOUNDS

CROSS-REFERENCE TO COMPANION APPLICATION

Application Ser. No. 08/541,983 [Attorney Docket No. 016800-043], now U.S. Pat. No. 5,663,270, filed Oct. 10, 1995 and assigned to the assignee hereof.

BACKGROUND OF THE INVENTION

1. Technical Field of the Invention

The present invention relates to novel cosmetic compositions for topical application, for the photoprotection of the skin and/or the hair against ultraviolet radiation (such compositions hereinafter simply designated "sunscreen," "sunscreen/cosmetic" or "photoprotective/sunscreen" compositions), and to the use of same for the cosmetic applications indicated above.

This invention more especially relates to the aforesaid sunscreen/cosmetic compositions comprising, in a cosmetically acceptable vehicle, carrier or diluent, typically an oil-in-water emulsion, combinatory immixture of at least two particular and unique sunscreen compounds, namely, on the one hand, 1,4-benzene [di-(3-methylidene-10-camphosulfonic)]acid and, on the other, a benzotriazole-substituted polyorganosiloxane. This admixture imparts enhanced solar protection factors to the subject compositions via an unexpected synergistic effect.

2. Description of the Prior Art

It is well known to this art that light radiation of wavelengths of from 280 nm to 400 nm promotes tanning of the human epidermis and that irradiation of wavelengths from 280 nm to 320 nm, i.e., UV-B, causes erythema and burning of the skin which can impair the development of a natural tan; hence, such UV-B radiation must thus be screened from the skin.

It is also known to this art that UV-A radiation, of wavelengths from 320 nm to 400 nm, which tans the skin, also adversely affects it, in particular in the event of sensitive skin or a skin which is continually exposed to solar radiation.

UV-A rays cause, in particular, a loss of elasticity of the skin and the appearance of wrinkles, promoting a premature aging thereof. Such irradiation promotes triggering of the erythematous reaction or enhances this reaction in certain individuals, and may even be the source of phototoxic or photoallergic reactions. Thus, it is desirable to also screen out UV-A radiation.

A wide variety of cosmetic compositions intended for the photoprotection (UV-A and/or UV-B) of human skin are known to this art.

These photoprotective/sunscreen compositions are typically oil-in-water emulsions (namely, a cosmetically acceptable vehicle, carrier or diluent comprising an aqueous continuous dispersing phase and an oily discontinuous dispersed phase) which contains, in various concentrations, one or more standard lipophilic and/or hydrophilic organic sunscreen compounds capable of selectively absorbing harmful or deleterious UV radiation. These sunscreen compounds (and the amounts thereof) are selected as a function of the desired sun protection factor (the sun protection factor (SPF) being expressed mathematically by the ratio of the irradiation time required to attain the erythema-forming threshold with the UV screening agent to the time required to attain the erythema-forming threshold in the absence of UV screening agent.

SUMMARY OF THE INVENTION

It has now unexpectedly and surprisingly been determined that a unique combination of two particular sunscreen compounds provides photoprotective/sunscreen compositions having protection factors which are markedly improved, and in all instances conspicuously superior to those which may be obtained, for an equal concentration of sunscreen compound and in a vehicle identical in nature, employing either of the sunscreen compounds alone.

Briefly, the present invention features novel photoprotective/cosmetic compositions comprising, in a cosmetically acceptable vehicle, diluent or carrier, (i) an effective amount of 1,4-benzene[di(3-methylidene-10-campho-sulphonic)] acid, optionally in a partially or completely neutralized form, as a first sunscreen compound, and (ii) as a second sunscreen compound, an effective amount of a benzotriazole-substituted silicone having one of the following formulae:

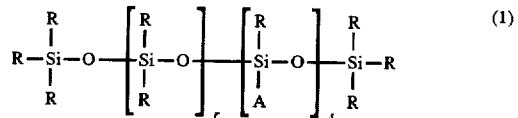

or

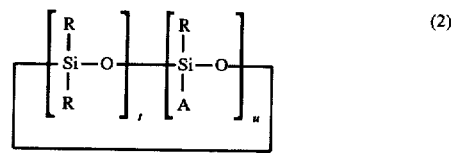

in which the radicals R, which may be identical or different, are each $C_1$–$C_{10}$ alkyl, phenyl or 3,3,3-trifluoropropyl radicals, at least 80% by number of the radicals R being methyl radicals; r is a integer ranging from 0 to 50, inclusive, and s is a integer ranging from 1 to 20, inclusive; u is an integer ranging from 1 to 6, inclusive, and t is an integer ranging from 0 to 10, inclusive, with the proviso that t+u is equal to or greater than 3; and the radical A is a monovalent radical bonded directly to a silicon atom, and which has the following formula (3):

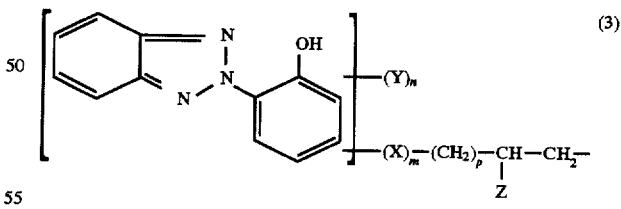

wherein the radicals Y, which may be identical or different, are each $C_1$–$C_8$ alkyl radicals, halogen atoms or $C_1$–$C_4$ alkoxy radicals, with the proviso that, in the latter event, two adjacent radicals Y on the same aromatic nucleus can together form an alkylidenedioxy radical in which the alkylidene group has from 1 to 2 carbon atoms; X is O or NH; Z is hydrogen or a $C_1$–$C_4$ alkyl radical; n is an integer ranging from 0 to 3, inclusive; m is 0 or 1; and p is an integer ranging from 1 to 10, inclusive.

The present invention also features the use of such compositions as, or for the formulation of, sunscreen/cosmetic compositions intended for the photoprotection of the skin and/or the hair against ultraviolet irradiation, in particular solar radiation.

The cosmetic treatment for the photoprotection of the skin and/or the hair against ultraviolet irradiation, in particular solar radiation, comprises topically applying thereto an effective amount of a sunscreen/cosmetic composition as described above.

DETAILED DESCRIPTION OF BEST MODE AND SPECIFIC/PREFERRED EMBODIMENTS OF THE INVENTION

More particularly according to the present invention, 1,4-benzene[di(3-methylidene-10-camphosulfonic)] acid and its various salts (compound (I)), described especially in FR-A-2,528,420 and FR-A-2,639,347, are sunscreen compounds which are known to this art per se (so-called broad spectrum screening agents) capable, indeed, of absorbing ultraviolet rays of wavelengths between 280 nm and 400 nm, with absorption maxima between 320 nm and 400 nm, in particular at about 345 nm. These screening compounds have the following structural formula (4):

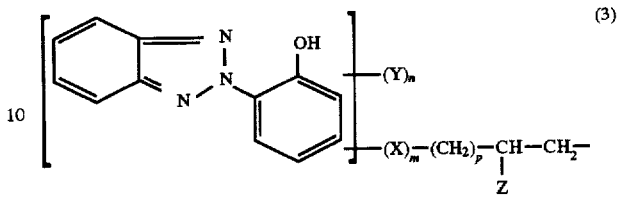

integer ranging from 1 to 6, inclusive, and t is an integer ranging from 0 to 10, inclusive, with the proviso that t+u is equal to or greater than 3; and the symbol A is a monovalent radical bonded directly to a silicon atom, and which has the following structural formula:

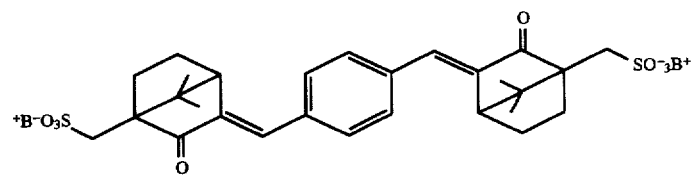

in which the radicals Y, which may be identical or different, are each $C_1$–$C_8$ alkyl radicals, halogen atoms or $C_1$–$C_4$ alkoxy radicals, with the proviso that, in the latter event, two adjacent radicals Y on the same aromatic nucleus may together form an alkylidenedioxy radical in which the alkylidene group has from 1 to 2 carbon atoms; X is O or NH; Z is hydrogen or a $C_1$–$C_4$ alkyl radical; n is an integer ranging from 0 to 3, inclusive; m is 0 or 1; and p is an integer ranging from 1 to 10, inclusive.

in which B is a hydrogen atom, an alkali metal or, alternatively, a radical $NH(R)_3^+$ in which the radicals R, which may be identical or different, are each a hydrogen atom, a $C_1$–$C_4$ alkyl or hydroxyalkyl radical or, alternatively, a group $M^{n+}/n$, wherein $M^{n+}$ is a polyvalent metal cation in which n is equal to 2 or 3 or 4, $M^{n+}$ preferably being a metal cation selected from among $Ca^{2+}$, $Zn^{2+}$, $Mg^{2+}$, $Ba^{2+}$, $Al^{3+}$ and $Zr^{4+}$. It should be appreciated that the compounds of formula (4) above may exist as "cis-trans" isomers about one or more double bonds and that all such isomers are within the scope of the present invention.

The benzotriazole-substituted silicones according to the present invention (compound (II)) belong to the general family of the benzotriazole silicones which is described especially in FR-A-2,642,968. As indicated above, the benzotriazole silicones according to the invention are those which have to the following structural formulae:

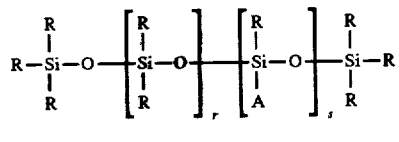

or

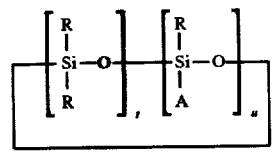

in which the radicals R, which may be identical or different, are each $C_1$–$C_{10}$ alkyl, phenyl and 3,3,3-trifluoropropyl radicals, at least 80% by number of the radicals R being methyl radicals; r is a integer ranging from 0 to 50, inclusive, and s is an integer ranging from 1 to 20, inclusive; u is an As is apparent from the above formula (3), the coupling of the linking radical —$(X)_m$—$(CH_2)_p$—$CH(Z)$—$CH_2$— to the benzotriazole nucleus thus ensures the bonding of the benzotriazole unit to a silicon atom of the silicone chain and this can occur in all the available positions offered by the two aromatic nuclei of the benzotriazole:

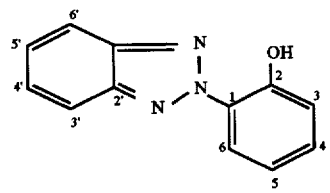

position (aromatic nucleus bearing the hydroxyl functional group) or in the 4' position (benzene nucleus adjacent to the triazole ring) , and even more preferably at the 3, 4 or 5 position. In a preferred embodiment of the invention, the coupling occurs at the 3 position.

Likewise, the attachment of the substituent Y can be at all the other available positions within the benzotriazole. However, preferably, this bonding is at the 3, 4, 4', 5 and/or 6 position. In a preferred embodiment of the invention, coupling is at the 5 position.

In the above formulae (1) and (2), the alkyl radicals may be linear or branched and are advantageously selected from among the methyl, ethyl, n-propyl, isopropyl, n-butyl, isobutyl, tert-butyl, n-amyl, isoamyl, neopentyl, n-hexyl, n-heptyl, n-octyl, 2-ethyehexyl and tert-octyl radicals. The alkyl radicals R which are preferred according to the invention are methyl, ethyl, propyl, n-butyl, n-octyl and 2-ethylhexyl radicals. Even more preferably, the radicals R are all methyl radicals.

Among the compounds of formula (1) or (2) above, preferred are those corresponding to the formula (1), namely, linear short-chain diorganosiloxanes.

Among the linear diorganosiloxanes which are within the scope of the present invention, more particularly preferred are the random or well-defined block derivatives having at least one, and even more preferably all, of the following characteristics:

R is alkyl and even more preferably methyl;

r ranges from 0 to 15, inclusive; s ranges from 1 to 5, inclusive;

n is not zero, and is preferably equal to 1, and Y is, in this case, selected from methyl, tert-butyl or a $C_1-C_4$ alkoxy;

Z is hydrogen or methyl;

m=0, or [m=1 and X=0];

p is equal to 1.

A family of compounds which are particularly suitable for the invention is that defined by the following general formula:

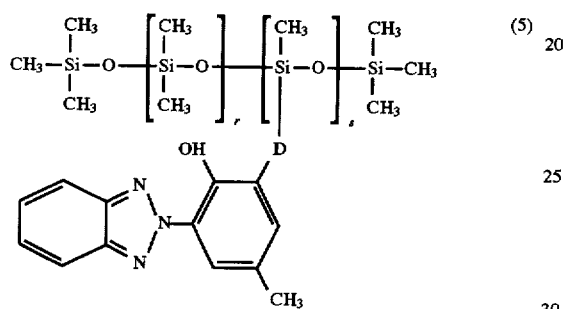

with $0 \leq r \leq 15$, preferably $0 \leq r \leq 10$ $1 \leq x \leq 5$, preferably $1 \leq s \leq 3$ and where D represents the divalent radical:

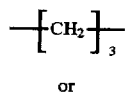

or

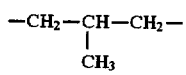

In a particularly preferred embodiment of the invention, the benzotriazole silicone has the general formula (5) in which:

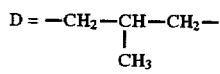

In another particularly preferred embodiment of the invention, the benzotriazole silicone has the general formula (5) in which:

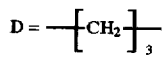

To prepare the silicone sunscreen agents of formulae (1) and (2), a conventional synthesis can be employed, i.e., a hydrosilylation reaction

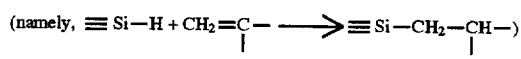

starting from the corresponding silicone in which, for example, all of the A radicals are hydrogen atoms. This starting silicone will hereinafter be designated the SiH-containing derivative. These SiH-containing derivatives are compounds which are well known in the silicone industry and are generally commercially available. They are, for example, described in U.S. Pat. Nos. 3,220,972, 3,697,473 and 4,340,709. This SiH-containing derivative can therefore be represented either by the following formula (1a):

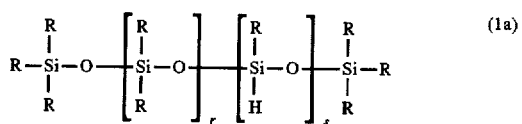

in which R, r and s are as defined above in respect of the formula (1), or by the following formula (2a):

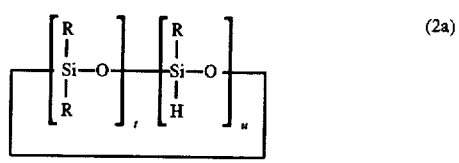

in which R, t and u are as defined above in respect of the formula (2).

This SiH-containing derivative of formula (1a) or (2a), is reacted, via conventional hydrosilylation reaction, carried out in the presence of a catalytically effective amount of a platinum catalyst, with an organic benzotriazole compound having the following formula (3a):

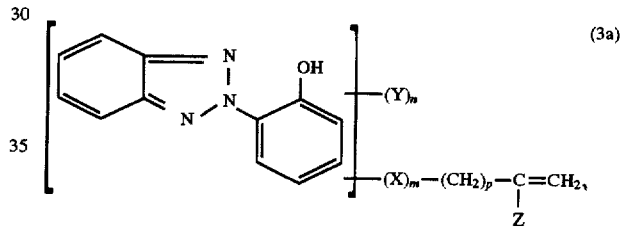

in which Y, X, Z, n, m and p are as defined above in respect of the formula (3).

Processes suitable for the preparation of the compounds of formula (3a) are especially described in U.S. Pat. Nos. 4,316,033 and 4,328,346.

In addition, the working conditions to be observed for conducting the hydrosilylation reaction between the compounds of formula (1a) or (2a) above and the compound of formula (3a) above are reported in aforesaid EP-0,392,883, hereby expressly incorporated by reference.

The compound (I) is advantageously present in the compositions according to the invention at a concentration ranging from 0.1% to 10%, preferably from 0.2% to 8%, by weight relative to the total weight of the composition and the compound (II) is advantageously present in amounts ranging from 0.1% to 10%, preferably from 0.2% to 8%, by weight, again relative to the total weight of the composition. Preferably, the overall content of the mixture between the compound (I) and the compound (II) does not exceed 15 of the total weight of the final composition.

From a practical point of view, the two compounds (I) and (II) above are of course preferably both present in the final composition in respective proportions chosen such that the synergistic effect, at the level of the sun protection factor conferred by the resulting combination, is optimal. The exact range of the weight ratios [compound (I)/compound (II)] in which this optimum synergistic effect is effectively achieved may vary slightly according to the total quantity of screening agents (I) and (II) used.

In addition, and in general, it will be noted that the concentrations and ratios of the compounds (I) and (II) are selected such that the sun protection factor of the final composition is preferably at least 2.

In a preferred embodiment of the present invention, the cosmetically acceptable vehicle, diluent or carrier in which the various compounds (I) and (II) are formulated is an oil-in-water type emulsion.

Of course, the sunscreen/cosmetic compositions according to the invention may contain one or more additional hydrophilic or lipophilic sunscreen agents active in the UVA and/or UVB range (absorbers), other than of course the two sunscreen compounds indicated above. Exemplary of such additional sunscreens are cinnamic derivatives, salicylic derivatives, camphor derivatives, triazine derivatives, benzophenone derivatives, dibenzoylmethane derivatives, β,β-diphenylacrylate derivatives, p-aminobenzoic acid derivatives, and the sunscreen polymers and sunscreen silicones described in WO-93/04665. Other examples of organic sunscreen agents are described in EP-A-0,487,404.

The compositions according to the invention may also contain artificial skin tanning and/or browning agents (self-tanning agents), such as, for example dihydroxyacetone (DHA).

The cosmetic compositions according to the invention may also contain pigments or alternatively nanopigments (mean primary particle size: generally ranging from 5 nm to 100 nm, preferably from 10 nm to 50 nm) of metal oxides, coated or otherwise, such as, for example, nanopigments of oxide of titanium (amorphous or crystallized in the form of rutile and/or anatase), iron, zinc, zirconium or cerium, which are all UV photoprotective agents per se well known to this art. Conventional coating agents are, moreover, alumina and/or aluminum stearate. Such nanopigments of metal oxides, coated or noncoated, are, in particular, described in EP-A-0,518,772 and EP-A-0,518,773.

The compositions of the invention may comprise, in addition, conventional cosmetic adjuvants and additives especially selected from among fatty substances, organic solvents, ionic or nonionic thickeners, demulcents, antioxidants, opacifiers, stabilizers, emollients, silicones, α-hydroxy acids, anti-foaming agents, moisturizing agents, vitamins, perfumes, preservatives, surfactants, fillers, sequestrants, polymers, propellants, alkalinizing or acidifying agents, colorants or any other ingredient customarily employed in cosmetics, in particular for the production of sunscreen/cosmetic compositions in the form of emulsions.

The fats or fatty substances may comprise an oil, a wax or mixtures thereof, and may also comprise fatty acids, fatty alcohols and esters of fatty acids. The oils may be selected from among animal, plant, mineral or synthetic oils and, especially from among petroleum jelly, paraffin oil, silicone oils, volatile or otherwise, isoparaffins, poly-α-olefins, fluorinated or perfluorinated oils. Likewise, the waxes may be selected from among animal, fossil, plant, mineral or synthetic waxes that are per se known to this art.

Exemplary organic solvents include the lower polyols and alcohols.

The thickeners may be selected, especially, from among crosslinked polyacrylic acids, guar gums and celluloses, modified or otherwise, such as hydroxypropylated guar gum, methylhydroxyethyl-cellulose, hydroxypropylmethylcellulose or hydroxyethylcellulose.

One skilled in the art will of course be careful to select this or these optional additional compounds and/or the quantities thereof such that the advantageous properties, in particular the synergistic effect, intrinsically a consequence of the binary combination in accordance with the invention are not, or not substantially, altered by such additions.

The compositions of the invention may be formulated according to techniques well known to this art, in particular those intended for the preparation of oil-in-water or water-in-oil emulsions.

The subject compositions may, in particular, be in the form of a simple or complex emulsion (O/W, W/O, O/W/O and W/O/W) such as a cream, a milk, a gel or a gel cream, of a powder, a solid stick and may be optionally packaged as an aerosol and provided in the form of a foam or a spray.

When it is an emulsion, the aqueous phase may comprise a nonionic vesicular dispersion prepared according to known processes (Bangham, Standish and Watkins, *J. Mol. Biol.*, 13, 238 (1965), FR 2,315,991 and FR 2,416,008).

The cosmetic composition of the invention are useful for protecting the human epidermis or the hair against the damaging effects of ultraviolet radiation, as sunscreen compositions or as makeup products.

When the cosmetic composition according to the invention are used for photoprotecting the human epidermis against UV rays, or as sunscreen compositions, they may be formulated as a suspension or a dispersion in solvents or fatty substances, or in the form of a nonionic vesicular dispersion or, alternatively, in the form of an emulsion, preferably of the oil-in-water type, such as a cream or a milk, in the form of an ointment, a gel, a gel cream, a solid stick, a stick, an aerosol foam or a spray.

When the cosmetic composition according to the invention are used for photoprotecting the hair, they may be formulated as a shampoo, a lotion, a gel, an emulsion, a nonionic vesicular dispersion, a lacquer for the hair and may constitute, for example, a rinse composition to be applied before or after shampooing, before or after dyeing or bleaching, before, during or after permanent waving or hair straightening, a hair-styling or treatment lotion or gel, a lotion or a gel for blow drying or for hair setting, a composition for permanent waving or for hair straightening, for dyeing or bleaching the hair.

When the subject compositions are used as a makeup product for the eyelashes, the eyebrows or the skin, such as a treatment cream for the epidermis, as foundation, lipstick, eyeshadow, blush, mascara or liner also called "eyeliner", they may be formulated in a solid or pasty, anhydrous or aqueous form, such as oil-in-water or water-in-oil emulsions, nonionic vesicular dispersions or alternatively suspensions.

For example, for the photoprotective/sunscreen formulations in accordance with this invention which comprise a carrier of the oil-in-water emulsion type, the aqueous phase (comprising, especially, the hydrophilic screening agents) generally constitutes from 50% to 95% by weight, preferably from 70% to 90% by weight, relative to the total formulation, the oily phase (comprising, especially, the lipophilic screening agents) from 5% to 50% by weight, preferably from 10% to 30% by weight, relative to the total formulation, and the (co)emulsifier(s) from 0.5% to 20% by weight, preferably from 2% to 10% by weight, relative to the total formulation.

The cosmetic treatment of the skin or of the hair to protect same against the deleterious effects of UV rays, especially those contained in solar radiation, comprises applying thereto an effective amount of a sunscreen/cosmetic composition as described above.

In order to further illustrate the present invention and the advantages thereof, the following specific examples are given, it being understood that same are intended only as illustrative and in nowise limitative.

EXAMPLE 1

Various photoprotective/sunscreen formulations were prepared in the form of an oil-in-water type emulsion and which contained (the quantities are expressed ink by weight relative to the total weight of the composition):

| Phase A: | |
| --- | --- |
| (a) A screening agent (II) which was a benzotriazole silicone (*), in an amount of | y% |
| (b) Mixture of glyceryl stearate and PEG-100 stearate marketed under the trademark "Arlacel 165" by ICI (emulsifier) | 1.5% |
| (c) Stearic acid marketed under the trademark "Stearine TP" by Stéarinerie Dubois | 2.75% |
| (d) Cetyl alcohol marketed under the trademark "Lorol C16" by Henkel (coemulsifier) | 0.5% |
| (e) Polydimethylsiloxane marketed under the trademark "Silbione 70 047 V 300" by Rhône-Poulenc | 0.5% |
| (f) $C_{12}$–$C_{15}$ alkyl benzoate marketed under the trademark "Finsolv TN" by Finetex | 13% |
| Phase B: | |
| (g) A screening agent (I) which was 1,4-benzene[di(3-methylidene-10-camphosulfonic)] acid, in an amount of | x% |
| (h) Pure glycerin Codex | 4% |
| (i) Potassium cetyl phosphate marketed under the trademark "Amphisol K" by Givaudan-Roure | 1% |
| (j) Crosslinked polyacrylic acid marketed under the trademark "Carbopol 980" by Goodrich | 0.3% |
| (k) Triethanolamine | qs pH 6.5–7 |
| (l) Water | qs 100% |
| Phase C: | |
| (m) Cyclopentadimethylsiloxane marketed under the trademark "DC 245 Fluid" by Dow Corning | 5% |
| (n) Preservatives | qs |

(*) Benzotriazole silicone having the formula:

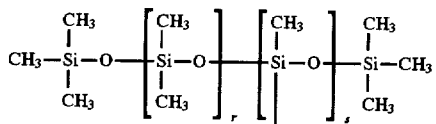

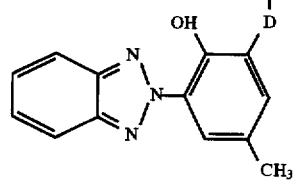

with
r=0
s=1
and

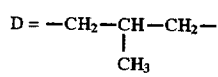

Each of these emulsions was prepared in the following manner: phases A and B were previously heated and homogenized at 80° C. Phase A was then dispersed, with rapid stirring, in phase B. The mixture was then allowed to cool, with gentle stirring. At 40° C., phase C was added.

For each of the formulations thus prepared, the sun protection factor (SPF) associated therewith was then determined. The measurement of the sun protection factor was carried out according to the following method (in vivo): these formulations were applied in an amount of 2 mg of product/cm$^2$ of skin, to the back of 10 human models, then the protected zones and the unprotected zones of the skin were subjected simultaneously to the action of a solar simulator marketed under the trademark "Xenon Multiport WG 320-UG 11"; the sun protection factor (SPF) was then mathematically calculated by the ratio of the irradiation time which was necessary to reach the erythematogenic threshold with the UV-screening agent (protected zone) to the time which was necessary to reach the erythematogenic threshold without UV-screening agent (unprotected zone).

The compositions of the various formulations and the results obtained, as mean sun protection factor (mean on the 10 models), are reported in the Table below:

TABLE

| Formulation Screening agent | 1 | 2 | 3 |
| --- | --- | --- | --- |
| (I) (x %) | — | 2 | 2 |
| (II) (y %) | 6 | — | 6 |
| (I) + (II) ((x + y) %) | 6 | 2 | 8 |
| Weight ratio y/x | — | — | 3 |
| Mean SPF | 5.2 | 3 | 15.8 |

These results clearly demonstrate the synergistic effect obtained with the composition 3 in accordance with the invention, the sun protection factor associated therewith being notably and significantly greater than the simple arithmetic sum of the sun protection factors of the corresponding comparative compositions containing only one screening agent.

EXAMPLE 2

A specific photoprotective/sunscreen composition in accordance with the invention was formulated as an oil-in-water type emulsion: the quantities are expressed in percentage by weight relative to the total weight of the composition.

| | |
| --- | --- |
| (a) 1,4-benzene[di(3-methylidene-10-camphosulfonic)] acid | 1% |
| (b) Benzotriazole silicone(*) | 3% |
| (c) mixture of cetyl stearyl alcohol and oxyethylenated cetyl stearyl alcohol containing 33 moles of EO (80/20) marketed under the trademark "Sinnovax AO" by Henkel | 7% |
| (d) Glycerol monostearate marketed under the trademark "Géléol Copeaux" by Gattefosse | 2% |
| (e) Cetyl alcohol marketed under the trademark "Lorol C 16" by Henkel | 1.5% |
| (f) Petroleum jelly | 15% |
| (g) Polydimethylsiloxane marketed under the trademark "Silbione 70 047 V 300" by Rhône-Poulenc | 1.5% |
| (h) Glycerin | 20% |

| | |
|---|---|
| (i) Triethanolamine | qs pH = 6.5 |
| (j) Preservatives | qs |
| (k) Water | qs 100% |

(*) Benzotriazole silicone having the formula:

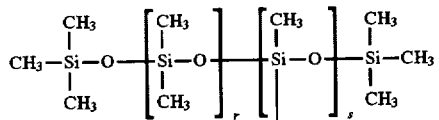

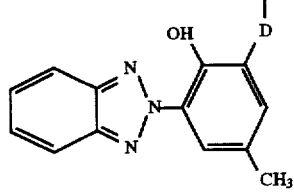

with
r=0
s=1
and

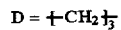

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition adopted for the photoprotection of human skin and/or hair, comprising a photoprotecting synergistically effective amount of (i) 1,4-benzene [di(3-methylidene-10-camphosulfonic)] acid, optionally either partially or totally neutralized, together with a photoprotecting synergistically effective amount of (ii) a benzotriazole-substituted polyorganosiloxane having one of the following structural formulae:

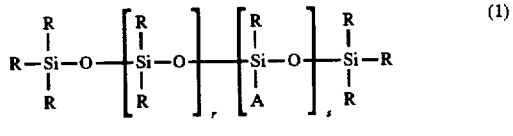

or

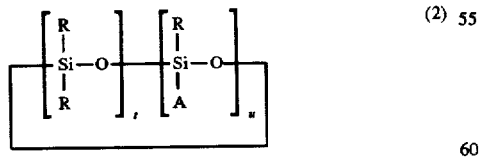

in which the radicals R, which may be identical or different, are each $C_1-C_{10}$ alkyl, phenyl and 3,3,3-trifluoropropyl radicals, at least 80% by number of the radicals R being methyl radicals; r is a integer ranging from 0 to 50, inclusive, and s is an integer ranging from 1 to 20, inclusive; u is an integer ranging from 1 to 6, inclusive, and t is an integer ranging from 0 to 10, inclusive, with the proviso that t+u is equal to or greater than 3; and the symbol A is a monovalent radical bonded directly to a silicon atom, and which has the following structural formula:

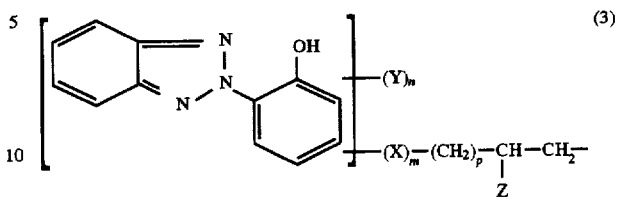

in which the radicals Y, which may be identical or different, are each $C_1-C_8$ alkyl radicals, halogen atoms or $C_1-C_4$ alkoxy radicals, with the proviso that, in the latter event, two adjacent radicals Y on the same aromatic nucleus may together form an alkylidenedioxy radical in which the alkylidene group has from 1 to 2 carbon atoms; X is O or NH; Z is hydrogen or a $C_1-C_4$ alkyl radical; n is an integer ranging from 0 to 3, inclusive; m is 0 or 1; and p is an integer ranging from 1 to 10, inclusive; in a cosmetically acceptable vehicle, carrier or diluent therefor.

2. The sunscreen/cosmetic composition as defined by claim 1, said benzotriazole-substituted polyorganosiloxane having the formula (1) wherein at least one of the following conditions is satisfied:

the radicals R are alkyl radicals;

r ranges from 0 to 15, inclusive;

s ranges from 1 to 15, inclusive;

n is other than zero;

Y is methyl, tert-butyl or $C_1-C_4$ alkoxy;

Z is hydrogen or methyl;

m=9, or;

p=1.

3. The sunscreen/cosmetic composition as defined by claim 2, all of said conditions being satisfied.

4. The sunscreen/cosmetic composition as defined by claim 1, said benzotriazole-substituted polyorganosiloxane having the structural formula (5):

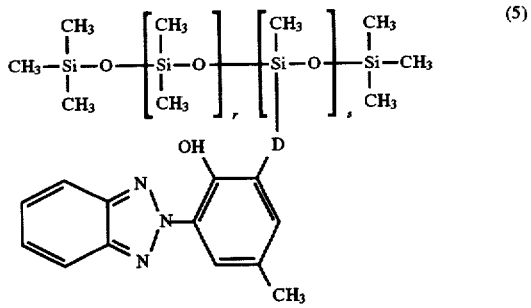

wherein $0 \leq r \leq 15$;

$1 \leq s \leq 5$;

and D is the divalent radical:

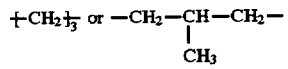

5. The sunscreen/cosmetic composition as defined by claim 4, wherein formula (5), r=0, s=1 and

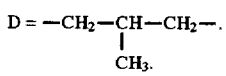
$$D = -CH_2-\underset{CH_3}{\underset{|}{CH}}-CH_2-.$$

6. The sunscreen/cosmetic composition as defined by claim 4, wherein formula (5), r=0, s=1 and D=—[CH$_2$]$_3$—.

7. The sunscreen/cosmetic composition as defined by claim 1, comprising from 0.1% to 10% by weight of said sulfonic acid compound.

8. The sunscreen/cosmetic composition as defined by claim 7, comprising from 0.2% to 8% by weight of said sulfonic acid compound.

9. The sunscreen/cosmetic composition as defined by claim 7, comprising from 0.1% to 10% by weight of said benzotriazole-substituted polyorganosiloxane.

10. The sunscreen/cosmetic composition as defined by claim 8, comprising from 0.2% to 8% by weight of said benzotriazole-substituted polyorganosiloxane.

11. The sunscreen/cosmetic composition as defined by claim 1, said sulfonic acid compound having the structural formula:

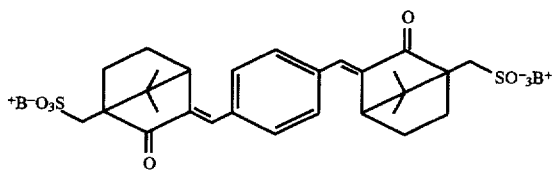

in which B is a hydrogen atom, an alkali metal or a radical $NH(R)_3^+$, wherein the radicals R, which may be identical or different, are each a hydrogen atom, a $C_1$–$C_4$ alkyl or hydroxyalkyl radical or a group $M^{n+}/n$, wherein $M^{n+}$ is a polyvalent metal cation in which n is equal to 2, 3 or 4.

12. The sunscreen/cosmetic composition as defined by claim 1, comprising an oil-in-water emulsion.

13. The sunscreen/cosmetic composition as defined by claim 1, comprising a water-in-oil emulsion.

14. The sunscreen/cosmetic composition as defined by claim 1, further comprising at least one additional hydrophilic or lipophilic organic UV-A and/or UV-B sunscreen.

15. The sunscreen/cosmetic composition as defined by claim 14, further comprising at least one cinnamic derivative, salicylic derivative, camphor derivative, triazine derivative, benzophenone derivative, dibenzoylmethane derivative, β,β-diphenylacrylate derivative, p-aminobenzoic acid derivative, sunscreen polymer, or sunscreen silicone.

16. The sunscreen/cosmetic composition as defined by claim 1, further comprising at least one active agent for the artificial tanning and/or browning of human skin.

17. The sunscreen/cosmetic composition as defined by claim 1, further comprising at least one cosmetically acceptable adjuvant or additive.

18. The sunscreen/cosmetic composition as defined by claim 17, said at least one adjuvant or additive comprising a fat, organic solvent, ionic or nonionic thickening agent, softener, antioxidant, anti-free-radical antioxidant, opacifying agent, stabilizing agent, emollient, silicone, a-hydroxy acid, anti-foaming agent, hydrating agent, vitamin, fragrance, preservative, surfactant, filler, sequestering agent, polymer, propellant, insect repellent, alkalinizing or acidifying agent, colorant, or mixture thereof.

19. The sunscreen/cosmetic composition as defined by claim 1, comprising a nonionic vesicle dispersion, emulsion, cream, milk, gel, cream gel, ointment, suspension, dispersion, powder, solid stick, foam or spray.

20. The sunscreen/cosmetic composition as defined by claim 1, comprising a makeup.

21. The sunscreen/cosmetic composition as defined by claim 20, comprising an anhydrous or aqueous solid or paste, emulsion, suspension, or dispersion.

22. The sunscreen/cosmetic composition as defined by claim 1, comprising a shampoo, lotion, gel, emulsion, nonionic vesicle dispersion, hair lacquer, or rinse.

23. The sunscreen/cosmetic composition as defined by claim 1, having a sun protection factor of at least 2.

24. A method for protecting human skin and/or hair against the deleterious effects of ultraviolet irradiation, comprising topically applying thereto an effective amount of the sunscreen/cosmetic composition as defined by claim 1.

25. A method for protecting human skin and/or hair against the deleterious effects of solar radiation, comprising topically applying thereto an effective amount of the sunscreen/cosmetic composition as defined by claim 1.

26. The sunscreen/cosmetic composition as defined by claim 1, further comprising at least one UV photoprotective pigment or nanopigment of a metal oxide.

27. The sunscreen/cosmetic composition as defined by claim 26, said at least one pigment or nanopigment comprising an oxide of titanium, zinc, iron, zirconium and/or cerium.

* * * * *